United States Patent
Pawar et al.

(10) Patent No.: US 9,624,222 B2
(45) Date of Patent: Apr. 18, 2017

(54) PROCESS FOR PREPARATION OF (2S, 5R)-7-OXO-6-SULPHOOXY-2-[((3R)-PYRROLIDINE-3-CARBONYL)-HYDRAZINO CARBONYL]-1,6-DIAZA-BICYCLO[3.2.1]OCTANCE

(71) Applicant: WOCKHARDT LIMITED, Aurangabad (IN)

(72) Inventors: Shivaji Sampatrao Pawar, Aurangabad (IN); Sunil Bhaginath Jadhav, Ahmednagar (IN); Amit Chandra Mishra, Lucknow (IN); Vipul Rane, Aurangabad (IN); Satish Bhawsar, Aurangabad (IN); Prasad Keshav Deshpande, Aurangabad (IN); Ravindra Dattatraya Yeole, Aurangabad (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 14/769,810

(22) PCT Filed: Oct. 12, 2013

(86) PCT No.: PCT/IB2013/059327
§ 371 (c)(1),
(2) Date: Aug. 22, 2015

(87) PCT Pub. No.: WO2014/135932
PCT Pub. Date: Sep. 12, 2014

(65) Prior Publication Data
US 2016/0002234 A1 Jan. 7, 2016

(30) Foreign Application Priority Data

Mar. 8, 2013 (IN) .......................... 715/MUM/2013

(51) Int. Cl.
*C07D 471/08* (2006.01)

(52) U.S. Cl.
CPC .................................. *C07D 471/08* (2013.01)

(58) Field of Classification Search
None
See application file for complete search history.

(56) References Cited

FOREIGN PATENT DOCUMENTS

IN   WO 2013030733 A1 *  3/2013  ......... A61K 31/4545

OTHER PUBLICATIONS

Peterson et al., Iterative High-Throughput Polymorphism Studies on Acetaminophen and an Experimentally Derived Structure for Form IIIAm. Chem. Soc., 124, 10958-10959, 10958 (2002).
Morissette et al., High-throughput crystallization: Polymorphs, salts, co-crystals and solvates of pharmaceutical solidsAdvanced Drug Delivery Reviews, 56, 275-300, 296 (2004).
Buar et al., Disappearing Polymorphs Revisited (pp. 6972-6993)Angew. Chem. Int. Ed., 54, 6972-6993 (2015).

* cited by examiner

*Primary Examiner* — Heidi Reese
(74) *Attorney, Agent, or Firm* — Bio INtellectual Property Services LLC (Bio IPS); O. (Sam) Zaghmout

(57) ABSTRACT

A process for preparation of (2S,5R)-7-oxo-6-sulphooxy-2-[((3R)-pyrrolidine-3-carbonyl)-hydrazino carbonyl]-1,6-di-aza-bicyclo[3.2.1]octane is disclosed comprising reacting a compound of Formula (II) with a compound of Formula (III) to obtain a compound of Formula (IV). The crystalline end-product is als claimed.

13 Claims, 1 Drawing Sheet

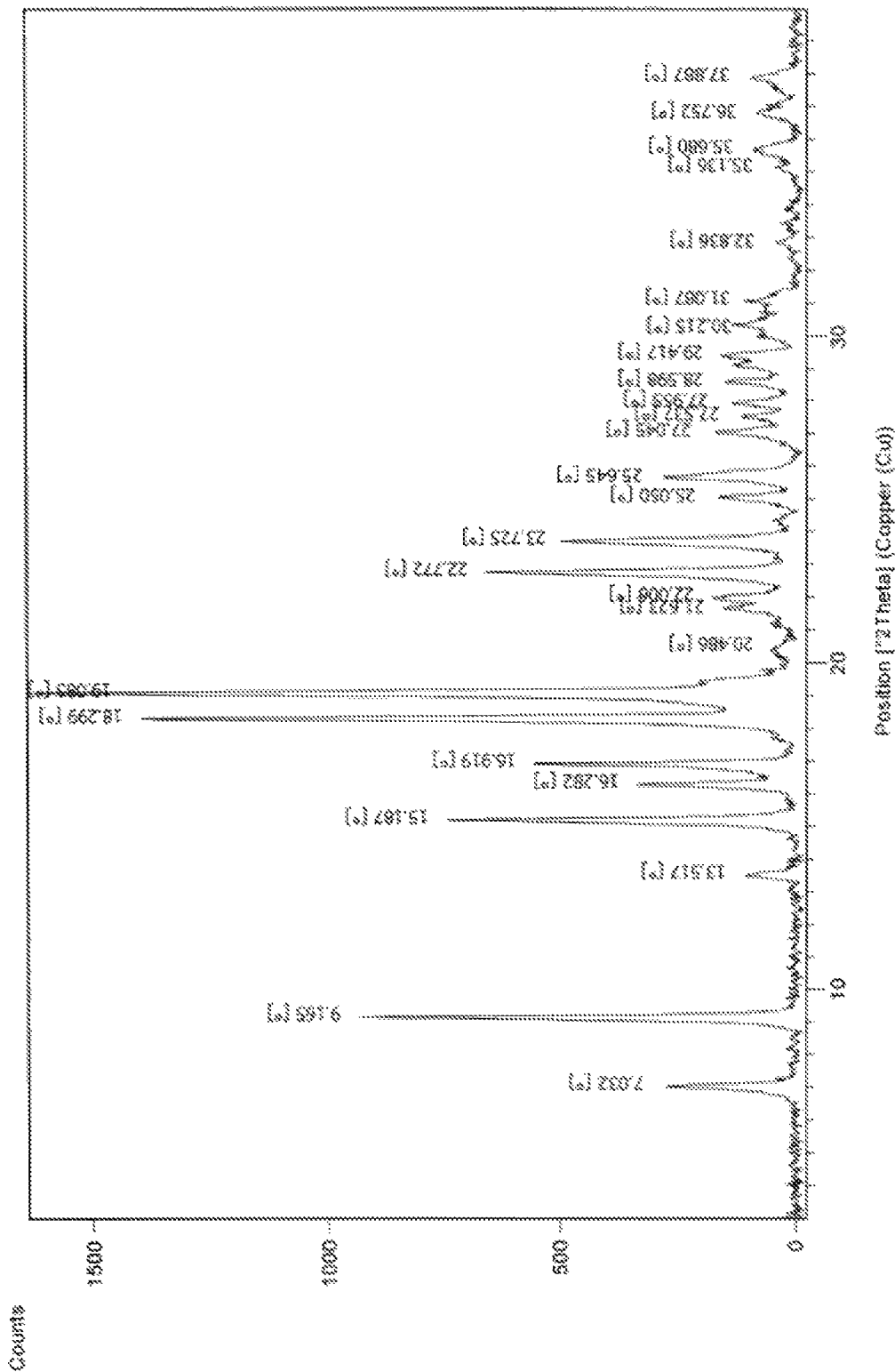

PROCESS FOR PREPARATION OF (2S, 5R)-7-OXO-6-SULPHOOXY-2-[((3R)-PYRROLIDINE-3-CARBONYL)-HYDRAZINO CARBONYL]-1,6-DIAZA-BICYCLO[3.2.1]OCTANCE

RELATED PATENT APPLICATIONS

This application claims benefit of Indian Patent Application No. 715/MUM/2013 filed on Mar. 8, 2013, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to a process for preparation of (2S,5R)-7-oxo-6-sulphooxy-2-[((3R)-pyrrolidine-3-carbonyl)-hydrazino carbonyl]-1,6-diaza-bicyclo[3.2.1]octane.

BACKGROUND OF THE INVENTION

A compound of Formula (I), chemically known as (2S, 5R)-7-oxo-6-sulphooxy-2-[((3R)-pyrrolidine-3-carbonyl)-hydrazino carbonyl]-1,6-diaza-bicyclo[3.2.1]octane has antibacterial properties and is disclosed in PCT/IB2012/054290.

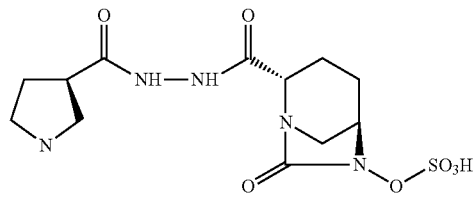

Formula (I)

SUMMARY OF THE INVENTION

In one general aspect, there is provided a process for preparation of a compound of Formula (I), comprising:

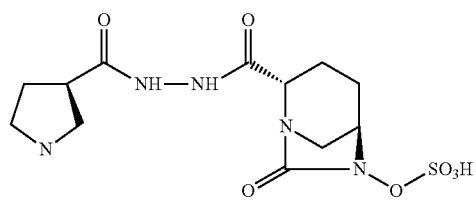

Formula (I)

(a) reacting a compound of Formula (II) with a compound of Formula (III) to obtain a compound of Formula (IV);

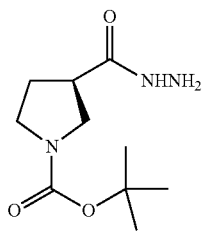

Formula (II)

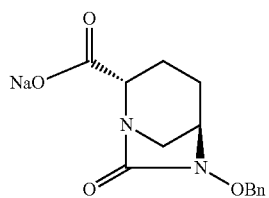

Formula (III)

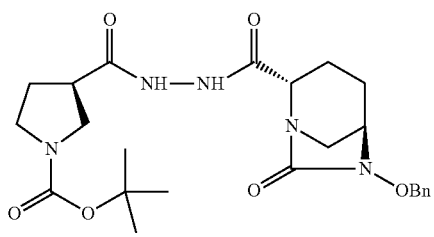

Formula (IV)

(b) hydrogenolysis of a compound of Formula (IV) to obtain a compound of Formula (V);

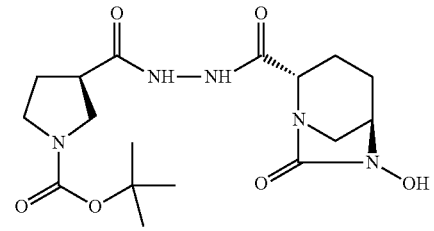

Formula (V)

(c) sulfonating a compound of Formula (V) to obtain a compound of Formula (VI); and

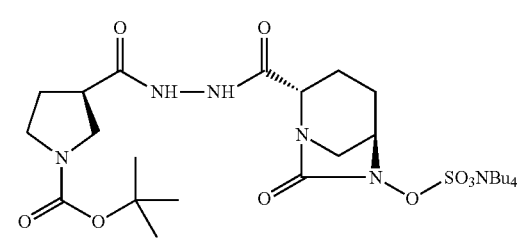

Formula (VI)

(d) converting a compound of Formula (VI) into a compound of Formula (I).

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety as if fully rewritten herein.

The term "HOBt" as used herein refers to 1-hydroxybenzotriazole.

The term "EDC" as used herein refers to 1-ethyl-3-(3-dimethylaminopropyl) carbodiimide.

In one general aspect, there is provided a process for preparation of a compound of Formula (I), comprising:

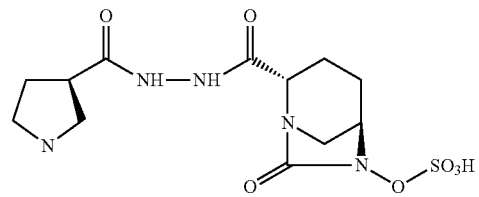

Formula (I)

(a) reacting a compound of Formula (II) with a compound of Formula (III) to obtain a compound of Formula (IV);

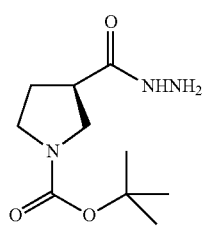

Formula (II)

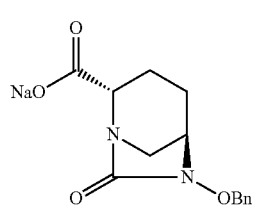

Formula (III)

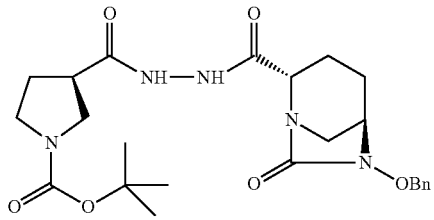

Formula (IV)

(b) hydrogenolysis of a compound of Formula (IV) to obtain a compound of Formula (V);

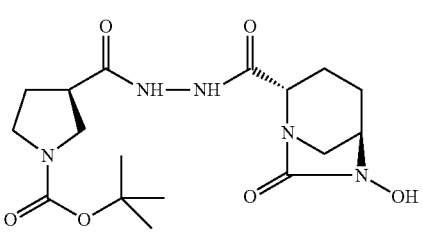

Formula (V)

(c) sulfonating a compound of Formula (V) to obtain a compound of Formula (VI); and

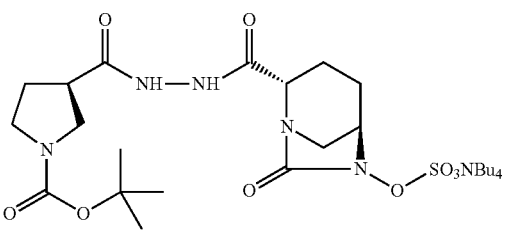

Formula (VI)

(d) converting a compound of Formula (VI) into a compound of Formula (I).

The compound of Formula (IV) is obtained by reacting a compound of Formula (II) with a compound of Formula (III). In some embodiments, this reaction is carried out in presence of 1-hydroxybenzotriazole. In some other embodiments, the compound of Formula (IV) is obtained by reacting a compound of Formula (II) with a compound Formula (III) in presence of 1-hydroxybenzotriazole and 1-ethyl-3-(3-dimethylaminopropyl)carbodiimide hydrochloride. In some embodiments, this reaction is carried out in water as a reaction solvent.

The compound of Formula (V) is obtained by hydrogenolysis of a compound of Formula (IV). The hydrogenolysis reaction can be carried out using a suitable hydrogenolysis agent. In some embodiments, hydrogenolysis of a compound of Formula (IV) to obtain a compound of Formula (V) is carried out in presence of a transition metal catalyst and a hydrogen source. In some other embodiments, the transition metal catalyst is palladium on carbon and hydrogen source is hydrogen gas. In some other embodiments, the hydrogenolysis reaction is carried out in presence of a suitable solvent such as an alcohol (for example, methanol). In some embodiments, the hydrogenolysis of a compound of Formula (IV) to obtain a compound of Formula (V) is carried out using 10% palladium on carbon catalyst, in presence of hydrogen gas, in methanol as a solvent.

The compound of Formula (VI) is obtained by sulfonating a compound of Formula (V). The sulfonation reaction can be carried out in presence of a suitable solvent. In some embodiments, the sulfonation of a compound of Formula (V) to obtain a compound of Formula (VI) is carried out by reacting a compound of Formula (V) with sulfur trioxide-pyridine complex, followed by treatment with tetra butyl ammonium hydrogen sulfate.

The compound of Formula (VI) is converted to a compound of Formula (I) in presence of a suitable reagent. In some embodiments, the compound of Formula (VI) is converted to a compound of Formula (I) by reacting a compound of Formula (VI) with trifluoroacetic acid.

In some embodiments, the compound of Formula (I) is prepared using a process described in Scheme 1.

27.04 (±0.2), 27.96 (±0.2), 29.41 (±0.2), 30.21 (±0.2), 35.68 (±0.2), 36.75 (±0.2), and 37.89 (±0.2) degrees 2 theta.

In some other embodiments, there is provided a compound of Formula (I) in a crystalline form and having an X-ray powder diffraction pattern comprising a peak selected from the group consisting of 7.03 (±0.2), 9.17 (±0.2), 15.19 (±0.2), 16.92 (±0.2), 18.30 (±0.2), 19.10 (±0.2), 22.77 (±0.2), and 23.72 (±0.2) degrees 2 theta.

In some other embodiments, there is provided a compound of Formula (I) in a crystalline form and having an X-ray powder diffraction pattern substantially the same as shown in FIG. 1.

In some embodiments, there is provided a process for the preparation of a compound of Formula (II), comprising:

(a) hydrogenolysis of a compound of Formula (VII) to obtain a compound of Formula (VIII)

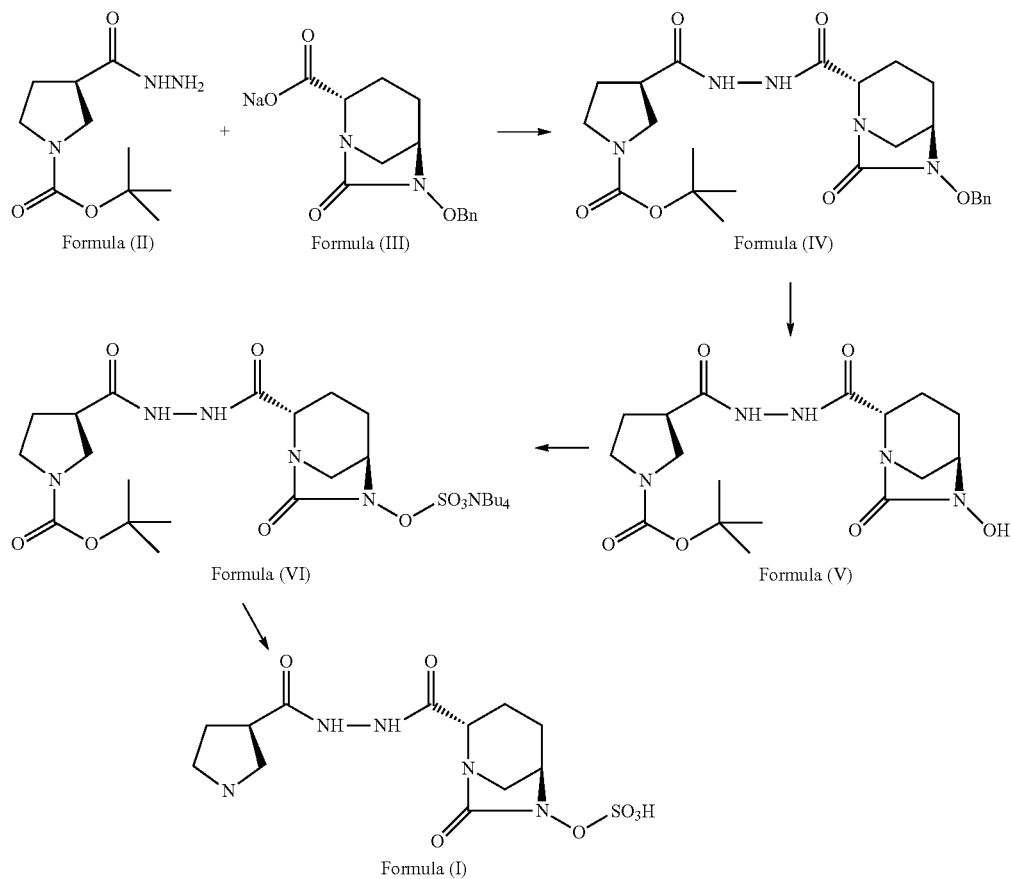

Scheme-1

In some embodiments, there is provided a compound of Formula (I) in crystalline form.

In some other embodiments, there is provided a compound of Formula (I) in a crystalline form and having an X-ray powder diffraction pattern comprising a peak selected from the group consisting of 7.03 (±0.2), 9.17 (±0.2), 13.52 (±0.2), 15.19 (±0.2), 16.28 (±0.2), 16.92 (±0.2), 18.30 (±0.2), 19.10 (±0.2), 20.49 (±0.2), 21.62 (±0.2), 22.01 (±0.2), 22.77 (±0.2), 23.72 (±0.2), 25.05 (±0.2) 25.64 (±0.2),

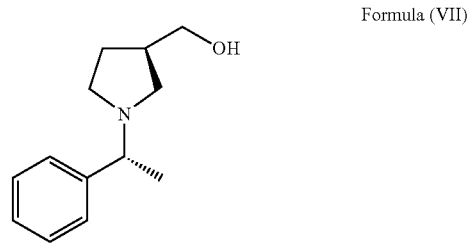

Formula (VII)

Formula (VIII)

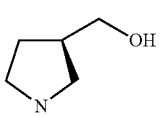

(b) converting a compound of Formula (VIII) to a compound of Formula (IX)

Formula (IX)

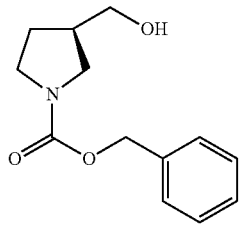

(c) oxidizing a compound of Formula (IX) to a compound of Formula (X),

Formula (X)

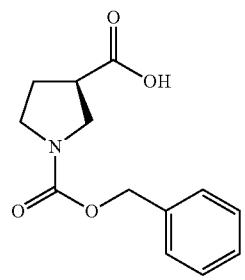

(d) esterfying a compound of Formula (X) to a compound of Formula (XI)

Formula (XI)

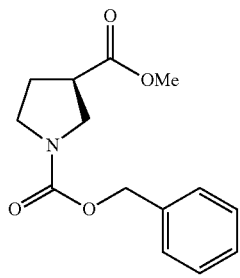

(e) hydrogenolysis of a compound of Formula (XI) to a compound of Formula (XII)

Formula (XII)

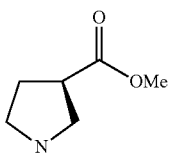

(f) converting a compound of Formula (XII) to a compound of Formula (XIII), and

Formula (XIII)

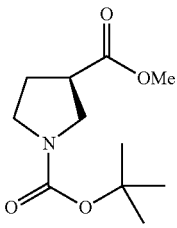

(g) converting a compound of Formula (XIII) to a compound of Formula (II).

A compound of Formula (VIII) is obtained by hydrogenolysis of a compound of Formula (VII). The hydrogenolysis reaction can be carried out using a suitable hydrogenolysis agent. In some embodiments, hydrogenolysis of a compound of Formula (VII) to obtain a compound of Formula (VIII) is carried out in presence of a transition metal catalyst and a hydrogen source. In some other embodiments, the transition metal catalyst is palladium on carbon and hydrogen source is hydrogen gas or ammonium formate. In some other embodiments, the hydrogenolysis reaction is carried out in presence of a suitable solvent such as an alcohol (for example, methanol). In some embodiments, the hydrogenolysis of a compound of Formula (VII) to obtain a compound of Formula (VIII) is carried out using 10% palladium on carbon catalyst, in presence of ammonium formate or hydrogen gas, in methanol as a solvent.

A compound of Formula (VIII) is then converted to a compound of Formula (IX) in presence of a suitable reagent such as benzyl chloroformate. The compound of Formula (IX) is treated with a suitable oxidizing reagent (such as Jone's reagent) to obtain a compound of Formula (X). The compound of Formula (X) is then esterified using a suitable reagent to obtain a compound of Formula (XI).

A compound of Formula (XII) is obtained by hydrogenolysis of a compound of Formula (XI). The hydrogenolysis reaction can be carried out using a suitable hydrogenolysis agent. In some embodiments, hydrogenolysis of a compound of Formula (XI) to obtain a compound of Formula (XII) is carried out in presence of a transition metal catalyst and a hydrogen source. In some other embodiments, the transition metal catalyst is palladium on carbon and hydrogen source is hydrogen gas or ammonium formate. In some other embodiments, the hydrogenolysis reaction is carried out in presence of a suitable solvent such as an alcohol (for example, methanol). In some embodiments, the hydrogenolysis of a compound of Formula (XI) to obtain a compound of Formula (XII) is carried out using 10% palladium on carbon catalyst, in presence of ammonium formate or hydrogen gas, in methanol as a solvent.

The compound of Formula (XII) is converted to a compound of Formula (XIII) in presence of di-tert-butyl carbonate and triethylamine in dichloromethane. The compound of Formula (II) is obtained by treating a compound of Formula (XIII) with hydrazine hydrate in ethanol. A schematic for synthesis of a compound of Formula (II) is given in Scheme-2.

Scheme - 2

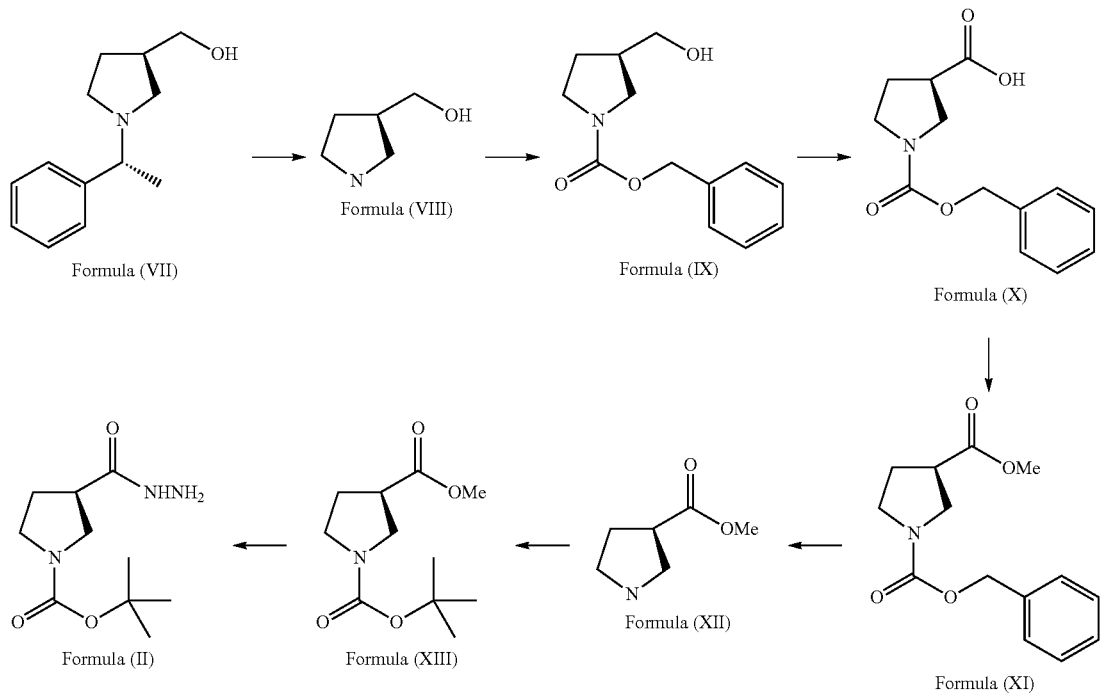

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of (R)—N-Boc-pyrrolidine-3-carboxylic acid hydrazide (II)

Step-1: Preparation of Formate salt of (R)-(pyrrolidin-3-yl)-methanol (VIII)

To a solution of (1R,3R)-[1-(1-phenylethyl)-pyrrolidin-3-yl]-methanol (VII, 124 gm, 0.60 mol) in methanol (2.5 L) was charged ammonium formate (114 gm, 1.81 mol) followed by 10% palladium on carbon catalyst (37 gm, 50% wet). The black suspension was stirred for 5 minutes and it was heated to a reflux temperature for 1 hour. As the TLC (20% methanol in chloroform) showed completion of reaction, the reaction mixture was cooled to room temperature. The catalyst was filtered at suction on celite and the catalyst was washed with methanol (500 ml). Evaporation of solvent under vacuum provided formate salt of (R)-(pyrrolidin-3-yl)-methanol (VIII) as an oily syrup in 73 gm quantity in 82% yield.

Analysis

Mass: (M+1): 102.0 for C5H11NO.HCOOH as a free base.

Step-2: Preparation of (R)-(1-Benzyloxycarbonyl-pyrrolidin-3-yl)-methanol (IX)

To a clear solution of formate salt of (R)-(pyrrolidin-3-yl)-methanol (VIII, 73 gm, 0.49 mol) in water (365 ml) was added tetrahydrofurane (365 ml) under stirring. To the reaction mixture was added 50% solution in toluene of benzyloxychloroformate (152 ml, 77 gm, 0.44 mol) followed by sodium bicarbonate (125 gm, 1.48 mol) as a solid. The reaction mixture was stirred overnight at 35° C. TLC (20% methanol in chloroform) showed completion of reaction. To the reaction mixture was added water (365 ml) and extracted twice with ethyl acetate (600 ml and 400 ml). Combined organic layer was given brine wash (500 ml) and organic layer was evaporated under vacuum to provide (R)-(1-benzyloxycarbonyl-pyrrolidin-3-yl)-methanol (IX) as oily syrup in 90 gm quantity in 79% yield.

Analysis

NMR: (CDCl3): 7.25-7.37 (m, 5H), 5.12 (s, 2H), 3.44-3.61 (m, 4H), 3.37-3.42 (m, 1H), 3.19 (q, 1H), 2.39-2.45 (m, 1H), 1.96-2.02 (m, 1H), 1.71 (q, 1H), 1.65 (s, 1H).

Mass (M+1): 236.2 for C13H17NO3.

Step-3: Preparation of (R)-1-Benzyloxycarbonyl-pyrrolidine-3-carboxylic acid (X)

To a solution of (R)-(1-benzyloxycarbonyl-pyrrolidin-3-yl)-methanol (IX, 80 gm, 0.34 mol) dissolved in acetone (800 ml) was added drop-wise under stirring Jones' reagent (200 ml, prepared by dissolving 53.4 gm $CrO_3$ in a solution prepared by mixing 46 ml $H_2SO_4$ and 140 ml water and final volume adjusted to 200 ml) at 20° C. till dark red colour persists of a solution and green coloured solid separates. The suspension was stirred for next 30 minutes. As the TLC (10% methanol in chloroform) showed complete conversion, isopropyl alcohol (100 ml) was added drop-wise to the reaction mixture, till green colour persists for 10 minutes. The suspension was filtered on the celite bed under suction and the solids were washed with fresh acetone (100 ml twice). The filtrate was evaporated under vacuum and to the residue was added saturated aqueous sodium bicarbonate solution (600 ml) till pH 8. The resultant mixture was extracted with ethyl acetate (400 ml) and layers were separated. Aqueous layer was adjusted to pH 2 by using 6N aqueous hydrochloric acid (125 ml). The reaction mixture was extracted with ethyl acetate (500 ml×2) and dried over sodium sulfate. Evaporation of solvent afforded (R)-1-benzyloxycarbonyl-pyrrolidine-3-carboxylic acid (X) in 67 gm quantity as an oily syrup in 79% yield.

Analysis:
NMR: (CDCl3): 9.25 (br s, 1H), 7.25-7.35 (m, 5H), 5.13 (s, 2H), 3.62-3.71 (m, 2H), 3.52-3.54 (m, 1H), 3.43-3.49 (m, 1H), 3.07-3.10 (m, 1H), 2.09-2.18 (m, 2H).
Mass (M−1): 248.1 for C13H15NO4.

Step-4: Preparation of (R)-Methyl-1-benzyloxycarbonyl-pyrrolidine-3-carboxylate (XI)

A solution of (R)-1-benzyloxycarbonyl-pyrrolidine-3-carboxylic acid (X, 67 gm, 0.26 mol) in methanolic HCl (670 ml) was stirred for 1.5 hour at 35° C. As TLC (10% methanol in chloroform) showed complete conversion, solvent was evaporated under vacuum and to the left over residue was charged saturated aqueous sodium bicarbonate solution (640 ml) under stirring carefully. The reaction mixture was extracted with ethyl acetate (400 ml×2). Combined organic layer was dried over sodium sulfate and evaporated under vacuum to provide (R)-methyl-1-benzyloxycarbonyl-pyrrolidine-3-carboxylate (XI) as an oily syrup in 64 gm quantity in 91% yield.

Analysis:
NMR (CDCl3): 7.25-7.36 (m, 5H), 5.12 (s, 2H), 3.70 (s, 3H), 3.53-3.63 (m, 3H), 3.42-3.51 (m, 1H), 3.03-3.42 (m, 1H), 2.12-2.16 (m, 2H).
Mass (M+1): 264.2 for C14H17NO4.

Step-5: Preparation of hydrochloride salt of (R)-methyl-pyrrolidine-3-carboxylate (XII)

A clear solution of (R)-methyl-1-benzyloxycarbonyl-pyrrolidine-3-carboxylate (XI, 64 gm, 0.24 mol) in methanol (640 ml) was transferred to a pressure reactor and was added 10% palladium on carbon catalyst (20 gm, 50% wet). The pH of reaction mixture was adjusted to 3 to 3.5 by addition of concentrated hydrochloric acid (25 ml). The reaction mixture was stirred under 100 psi pressure of hydrogen gas for 1.5 hour. As TLC (50% ethyl acetate in hexanes) showed completion of reaction, the catalyst was filtered on a celite bed under suction. The catalyst was washed with fresh methanol (100 ml). Evaporation of solvent under vacuum afforded hydrochloride salt of (R)-methyl-pyrrolidine-3-carboxylate (XII) in 40 gm quantity in quantitative yield, which was used for next reaction immediately.

Analysis
Mass (M+1): 130.0 for C6H11NO2 as a free base.

Step-6: Preparation of (R)-Methyl-1-tert-butoxycarbonyl-pyrrolidine-3-carboxylate (XIII)

The hydrochloride salt of (R)-methyl-pyrrolidine-3-carboxylate obtained as above (XII, 40 gm, 0.24 mol) was suspended in dichloromethane (400 ml) and cooled to 0° C. and to it was added di-tert-butyl carbonate (55 ml, 0.24 mol), followed by triethylamine (101 ml, 0.72 mol) under stirring. The reaction mixture was stirred for 1 hour and as TLC (50% ethyl acetate in hexane) showed completion of reaction, it was diluted with dichloromethane (200 ml) followed by water (400 ml) and the suspension was filtered on celite bed and washed with dichloromethane (200 ml). Layers in the filtrate were separated and organic layer was evaporated under vacuum to provide a residue which was purified on short silica gel column to afford (R)-methyl-1-tert-butoxycarbonyl-pyrrolidine-3-carboxylate (XIII) as colourless oil in 52 gm quantity in 95% yield.

Analysis
NMR: (CDCl3): 3.70 (s, 3H), 3.40-3.60 (m, 3H), 3.30-3.40 (m, 1H), 3.00-3.10 (m, 1H), 2.09-2.20 (br m, 2H), 1.45 (s, 9H).
Mass (M+1): 230.2 for C11H19NO4.
Chiral purity by HPLC: 99.87%

Step-7: Preparation of (R)—N-Boc-pyrrolidine-3-carboxylic acid hydrazide (II)

To a solution of (R)-methyl-1-tert-butoxycarbonyl-pyrrolidine-3-carboxylate (XIII, 52 gm, 0.22 mol) in ethanol (520 ml), was charged hydrazine hydrate (57 ml, 1.13 mol). The reaction mixture was stirred for 2.5 hours at 80° C. As TLC showed complete conversion, solvent was evaporated under vacuum. To the residue was added water (500 ml) and it was extracted with 10% methanolic chloroform twice (400 ml and 300 ml). Combined organic layer was dried over sodium sulfate and evaporated under vacuum to provide (R)—N-Boc-pyrrolidine-3-carboxylic acid hydrazide (II) as oil in 54 gm quantity in quantitative yield.

Analysis
NMR: (CDCl3): 7.03 (br s, 1H), 3.91 (br s, 2H), 3.41-3.68 (m, 3H), 3.29-3.40 (m, 1H), 2.81 (br d, 1H), 2.03-2.14 (m, 2H), 1.45 (s, 9H).
Mass (M+1): 230.2 for C10H19N3O3.
Chiral purity by HPLC: 99.88%

Example 2

Preparation of (2S,5R)-7-oxo-6-sulphooxy-2-[((3R)-pyrrolidine-3-carbonyl)-hydrazino carbonyl]-1,6-diaza-bicyclo[3.2.1]octane (I)

Step-1: Preparation of (2S,5R)-6-benzyloxy-7-oxo-2-[((3R)—N-Boc-pyrrolidine-3-carbonyl)-hydrazino carbonyl]-1,6-diaza-bicyclo[3.2.1]octane (IV)

Sodium (2S,5R)-6-benzyloxy-7-oxo-bicyclo[3.2.1]-1,6-diaza octane-2-carboxylate (III, 67 gm, 0.22 mol; prepared using a method disclosed in Indian Patent Application No 699/MUM/2013) was dissolved in water (1.0 L) to obtain a clear solution at 35° C. To the clear solution, was added successively, (R)—N-Boc-pyrrolidine-3-carboxylic acid hydrazide (II, 54 gm, 0.23 mol), EDC hydrochloride (65 gm, 0.33 mol), and HOBt (30.2 gm, 0.22 mol) followed by water (0.14 L) under stirring at 35° C. Resulting suspension was stirred at 35° C. for 18 hours. As maximum precipitation was reached, TLC (methanol:chloroform 1:9) showed completion of reaction. The precipitated white solid was filtered under suction and the wet cake was stirred with additional water (1.0 L) for 3 hours. The suspension was filtered and the cake was washed with water (200 ml), air dried for overnight to furnish (2S, 5R)-6-benzyloxy-7-oxo-2-[((3R)—N-Boc-pyrrolidine-3-carbonyl)-hydrazinocarbonyl]-1,6-diaza-bicyclo[3.2.1]octane (IV) as a white powder in 95 gm quantity in 88% yield.

Analysis

NMR: (CDCl3): 8.61 (br s, 1H), 8.21 (br d, 1H), 7.36-7.42 (m, 5H), 5.03 (d, 1H), 4.90 (d, 1H), 3.98 (d, 1H), 3.60-3.70 (m, 1H), 3.48-3.52 (m, 2H), 3.31-3.35 (m, 2H), 3.04-3.12 (m, 2H), 2.98 (t, 1H), 2.26-2.30 (m, 1H), 2.11 (br s, 2H), 1.91-1.99 (m, 2H), 1.59-1.61 (m, 1H), 1.43 (s, 9H).

Mass: (M−1)=486.3 for C24H33N5O6

HPLC purity: 98.89%

Step-2: Preparation of (2S,5R)-6-hydroxy-7-oxo-2-[((3R)—N-Boc-pyrrolidine-3-carbonyl)-hydrazino carbonyl]-1,6-diaza-bicyclo[3.2.1]octane (V)

A compound, (2S,5R)-6-benzyloxy-7-oxo-2-[((3R)—N-Boc-pyrrolidine-3-carbonyl)-hydrazinocarbonyl]-1,6-diaza-bicyclo[3.2.1]octane (IV, 87 gm, 0.17 mol) was dissolved in methanol (0.87 L) to obtain a clear solution. To this solution, was added 10% Pd—C (17 gm, 50% wet) catalyst. The suspension was stirred for 3 hours under 100 PSI hydrogen pressure at 35° C. As the reaction showed completion on TLC (TLC system methanol: chloroform 1:9), the catalyst was filtered through celite bed under suction. The celite bed was washed with methanol (200 ml). The filtrate was evaporated under vacuum below 40° C. to provide a crude solid (2S,5R)-6-hydroxy-7-oxo-2-[((3R)—N-Boc-pyrrolidine-3-carbonyl)-hydrazinocarbonyl]-1,6-diaza-bicyclo[3.2.1]octane (V) in 72 gm quantity in a quantitative yield. This product being unstable, was used immediately for the next reaction.

Analysis

NMR: (DMSO-d6): 9.70-9.90 (m, 2H), 4.06-4.08 (m, 1H), 3.76 (d, 1H), 3.58 (br s, 1H), 3.35-3.50 (m, 1H), 3.10-3.40 (m, 4H), 2.97 (br d, 2H), 1.79-2.04 (m, 4H), 1.73-1.81 (m, 1H), 1.53-1.71 (m, 1H), 1.37 (s, 9H).

Mass: (M−1): 396.2 for C17H27N5O6

HPLC purity: 90.99%

Step-3: Preparation of Tetrabutyl ammonium salt of (2S,5R)-6-sulfooxy-7-oxo-2-[((3R)—N-Boc-pyrrolidine-3-carbonyl)-hydrazino carbonyl]-1,6-diaza-bicyclo[3.2.1]octane (VI)

A solution of (2S,5R)-6-hydroxy-7-oxo-2-[((3R)—N-Boc-pyrrolidine-3-carbonyl)-hydrazinocarbonyl]-1,6-diaza-bicyclo[3.2.1]octane (V, 67 gm, 0.16 mol) in pyridine (0.67 L) was charged sulfur trioxide-pyridine complex (134 gm, 0.84 mol) under stirring at 35° C. The reaction mixture was stirred for 16 hours. The suspension was filtered through celite bed, and the bed was washed with dichloromethane (500 ml). The filtrate was evaporated to dryness below 40° C. to provide a residue. To the residue was added 0.5 M aqueous potassium dihydrogen phosphate (1.7 L). The reaction mixture was stirred for 15 minutes at 35° C. and then extracted with dichloromethane (1 L×2). Layers were separated. To the aqueous layer was added solid tetrabutyl ammonium hydrogen sulfate (51 gm, 0.0.15 mol) and stirring was continued for 2 hours at 35° C. The reaction mixture was extracted with dichloromethane (0.7 L×2). Layers were separated. Combined organic layer was evaporated under vacuum below 40° C. to provide tetrabutyl ammonium salt of (2S,5R)-6-sulfooxy-7-oxo-2-[((3R)—N-Boc-pyrrolidine-3-carbonyl)-hydrazino carbonyl]-1,6-diaza-bicyclo[3.2.1]octane (VI) as a white solid in 106 gm quantity in 87% yield.

Analysis

NMR: (CDCl3): 8.63-8.70 (m, 2H), 5.28 (s, 1H), 4.23 (br s, 1H), 3.97 (d, 1H), 3.10-3.40 (m, 1H), 3.49 (t, 2H), 3.22-3.40 (m, 10H), 3.09 (br s, 2H), 12.28-2.33 (m, 1H), 2.20-2.17 (m, 5H), 1.80-1.90 (m, 2H), 1.57-1.71 (m, 9H), 1.33-1.46 (m, 18H), 0.98 (t, 12H).

Mass: (M−1): 476.4 as a free sulfonic acid C17H26N5O9S.N(C4H9)4;

HPLC purity: 98.34%

Step-4: Synthesis of (2S,5R)-7-oxo-6-sulphooxy-2-[((3R)-pyrrolidine-3-carbonyl)-hydrazino carbonyl]-1,6-diaza-bicyclo[3.2.1]octane (I)

The tetra-butyl ammonium salt of (2S,5R)-6-sulfooxy-7-oxo-2-[((3R)—N-Boc-pyrrolidine-3-carbonyl)-hydrazinocarbonyl]-1,6-diaza-bicyclo[3.2.1]octane (VI, 110 gm, 0.15 mol) was dissolved in dichloromethane (275 ml) and to the clear solution was slowly added trifluoroacetic acid (275 ml) at 0 to 5° C. The reaction mixture was stirred between 0 to 5° C. for additional 1 hour. The solvent and excess trifluoroacetic acid was evaporated under vacuum below 40° C. to approximately ⅓ of its original volume to provide pale yellow oily residue. Oily residue was stirred with diethyl ether (1.0 L) to provide a suspension. The precipitate was filtered under suction and transferred to round bottom flask, and again stirred with diethyl ether (1.0 L) for 30 minutes. The suspension was filtered under suction to provide a crude solid. The crude solid was charged in a round bottom flask and to it was added dichloromethane (1.0 L). The pH of suspension was adjusted to 7.0 to 7.5 by adding triethylamine. The resulting suspension was filtered under suction and the wet cake was washed with dichloromethane (200 ml) to provide a crude solid. The crude solid was dried under vacuum below 40° C. to furnish 61 gm crude mass. The crude mass was dissolved in water (61 ml) under stirring and to the clear solution, was added isopropyl alcohol (580 ml). The suspension was stirred for 70 hours and filtered under suction. The wet cake was washed with isopropyl alcohol (100 ml) and dried under vacuum below 40° C. to provide crystalline (2S,5R)-7-oxo-6-sulphooxy-2-[((3R)-pyrrolidine-3-carbonyl)-hydrazino carbonyl]-1,6-diaza-bicyclo[3.2.1]octane (I) in 33 gm quantity in 60% yield.

Analysis

NMR: (DMSO-d6)=9.25 (br s, 3H), 4.00 (br s, 1H), 3.82 (d, 1H), 3.22-3.37 (m, 5H), 3.15-3.22 (m, 3H), 3.05-3.12 (m, 2H), 2.95-3.05 (m, 1H), 2.12-2.22 (m, 1H), 1.94-2.08 (m, 2H), 1.82-1.90 (br s, 1H), 1.66-1.78 (m, 1H), 1.54-1.64 (m, 1H).

Mass: (M−1): 376.3 for C12H19N5O7S

HPLC purity: 96.64%

Specific rotation: $[\alpha]^{25}_D$: −47.5° (c 0.5, water)

X-ray powder diffraction pattern comprising peak at (2 Theta Values): 7.03 (±0.2), 9.17 (±0.2), 13.52 (±0.2), 15.19

(±0.2), 16.28 (±0.2), 16.92 (±0.2), 18.30 (±0.2), 19.10 (±0.2), 20.49 (±0.2), 21.62 (±0.2), 22.01 (±0.2), 22.77 (±0.2), 23.72 (±0.2), 25.05 (±0.2) 25.64 (±0.2), 27.04 (±0.2), 27.96 (±0.2), 29.41 (±0.2), 30.21 (±0.2), 35.68 (±0.2), 36.75 (±0.2), and 37.89 (±0.2).

Typical X-ray analysis was performed as follows. Pass the test substance through sieve #100 BSS or gently grind it with a mortar and pestle. Place the test substance uniformly on a sample holder having cavity surface on one side, press the sample and cut into thin uniform film using a glass slide in such a way that the surface of the sample should be smooth and even. Record the X-ray diffractogram using the following instrument parameters.

| Instrument | X-Ray Diffractometer (PANalytical, Model X'Pert Pro MPD) |
| --- | --- |
| Target source | Cu k (α) |
| Anti-scattering slit (Incident beam) | 1° |
| Programmable Divergent slit | 10 mm (fixed) |
| Anti-scattering slit (Diffracted beam) | 5.5 mm |
| Step width | 0.02° |
| Voltage | 40 kV |
| Current | 40 mA |
| Time per step | 30 seconds |
| Scan range | 3 to 40° |

We claim:

1. A process for preparation of a compound of Formula (I), comprising:

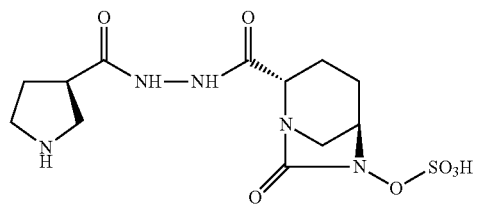

Formula (I)

(a) reacting a compound of Formula (II) with a compound of Formula (III) in the presence of a solvent to obtain a compound of Formula (IV);

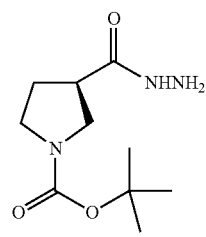

Formula (II)

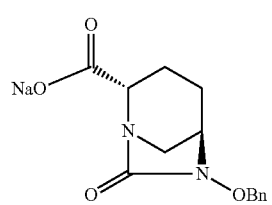

Formula (III)

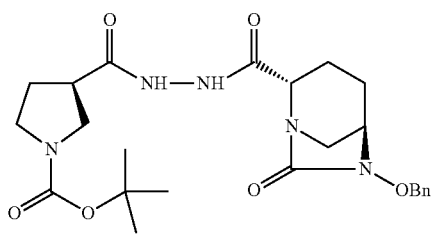

Formula (IV)

(b) hydrogenolysis of the compound of Formula (IV) to obtain a compound of Formula (V);

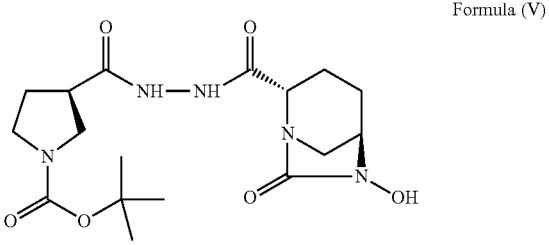 [SMILES: CC(C)(C)OC(=O)N1CC[C@@H](C(=O)NNC(=O)[C@@H]2CC[C@@H]3CN2C(=O)N3O)C1]

Formula (V)

(c) sulfonating the compound of Formula (V) to obtain a compound of Formula (VI); and

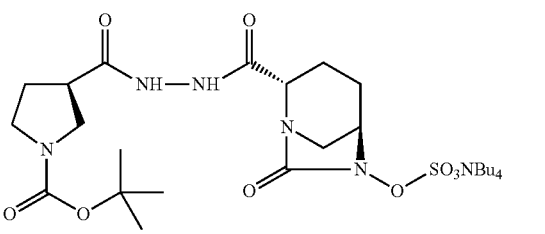

Formula (VI)

(d) converting the compound of Formula (VI) into the compound of Formula (I).

2. The process according to claim 1, wherein the reacting of the compound of Formula (II) with the compound of Formula (III) to obtain the compound of Formula (IV) is carried out in the presence of 1-hydroxybenzotriazole and 1-ethyl-3-(3-dimethylaminopropyl) carbodiimide hydrochloride.

3. The process according to claim 1, wherein the reacting of the compound of Formula (II) with the compound of Formula (III) to obtain the compound of Formula (IV) is carried out in the presence of water as the solvent.

4. The process according to claim 1, wherein the hydrogenolysis of the compound of Formula (IV) to obtain the compound of Formula (V) is carried out in the presence of a transition metal catalyst and a hydrogen source.

5. The process according to claim 4, wherein the transition metal catalyst is palladium on carbon and the hydrogen source is hydrogen gas.

6. The process according to claim 1, wherein the sulfonating of the compound of Formula (V) to obtain the compound of Formula (VI) is carried out by reacting the compound of Formula (V) with sulfur trioxide—pyridine complex, followed by treatment with tetra butyl ammonium hydrogen sulfate.

7. The process according to claim 1, wherein the compound of Formula (VI) is converted to the compound of Formula (I) by reacting the compound of Formula (VI) with trifluoroacetic acid.

8. A compound of Formula (I)

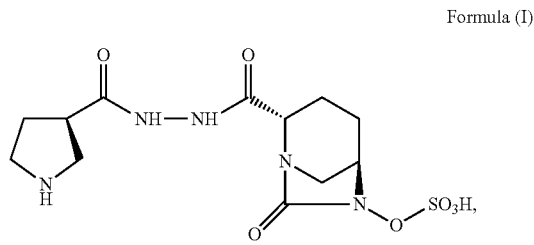 [SMILES: O=C(NNC(=O)[C@@H]1CC[C@@H]2CN1C(=O)N2OS(=O)(=O)O)[C@@H]1CCNC1]

Formula (I)

wherein the compound is in crystalline form.

9. The compound of Formula (I) according to claim 8, wherein the compound has an X-ray powder diffraction pattern comprising a peak selected from the group consisting of 7.03 (±0.2), 9.17 (±0.2), 13.52 (±0.2), 15.19 (±0.2), 16.28 (±0.2), 16.92 (±0.2), 18.30 (±0.2), 19.10 (±0.2), 20.49 (±0.2), 21.62 (±0.2), 22.01 (±0.2), 22.77 (±0.2), 23.72 (±0.2), 25.05 (±0.2) 25.64 (±0.2), 27.04 (±0.2), 27.96 (±0.2), 29.41 (±0.2), 30.21 (±0.2), 35.68 (±0.2), 36.75 (±0.2), and 37.89 (±0.2) degrees 2 theta.

10. The compound of Formula (I) according to claim 8, wherein the compound has an X-ray powder diffraction pattern comprising a peak selected from the group consisting of 7.03 (±0.2), 9.17 (±0.2), 15.19 (±0.2), 16.92 (±0.2), 18.30 (±0.2), 19.10 (±0.2), 22.77 (±0.2), and 23.72 (±0.2) degrees 2 theta.

11. The compound of Formula (I) according to claim 8, wherein the compound has an X-ray powder diffraction pattern substantially as shown in FIG. 1.

12. The compound according to claim 8, wherein the compound of Formula (I) is obtained according to the process of claim 1.

13. The compound according to claim 8, wherein the compound of Formula (I) has a purity of at least about 96% as determined by HPLC.

* * * * *